(12) United States Patent
Ouyang et al.

(10) Patent No.: US 7,191,918 B2
(45) Date of Patent: Mar. 20, 2007

(54) DOSAGE COUNTING DEVICES

(75) Inventors: Tianhong Ouyang, Chapel Hill, NC (US); Geoff Brace, Raleigh, NC (US)

(73) Assignee: Bespak PLC, Norfolk (GB)

( * ) Notice: Subject to any disclaimer, the term of this patent is extended or adjusted under 35 U.S.C. 154(b) by 444 days.

(21) Appl. No.: 10/468,810

(22) PCT Filed: Feb. 22, 2002

(86) PCT No.: PCT/GB02/00814

§ 371 (c)(1),
(2), (4) Date: Mar. 9, 2004

(87) PCT Pub. No.: WO02/067844

PCT Pub. Date: Sep. 6, 2002

(65) Prior Publication Data

US 2004/0149773 A1    Aug. 5, 2004

(30) Foreign Application Priority Data

Feb. 23, 2001  (GB) ................................ 0104557.4

(51) Int. Cl.
*B67D 5/22* (2006.01)
(52) U.S. Cl. .................... 222/36; 128/205.23
(58) Field of Classification Search ............... 222/36, 222/23, 30, 32, 38; 128/200.23, 205.23, 128/203.12, 203.15; 604/58
See application file for complete search history.

(56) References Cited

U.S. PATENT DOCUMENTS

| | | | |
|---|---|---|---|
| 4,817,822 A * | 4/1989 | Rand et al. .................... 222/38 |
| 5,228,586 A | 7/1993 | Fuchs | |
| 5,421,482 A | 6/1995 | Garby et al. | |
| 5,482,030 A * | 1/1996 | Klein .................... 128/200.23 |
| 5,611,444 A | 3/1997 | Garby et al. | |
| 5,687,710 A | 11/1997 | Ambrosio et al. | |
| 5,718,355 A | 2/1998 | Garby et al. | |
| 5,740,972 A | 4/1998 | Matthew | |
| 5,799,651 A * | 9/1998 | Garby et al. ........... 128/200.23 |
| 5,829,434 A | 11/1998 | Ambrosio et al. | |
| 5,988,496 A * | 11/1999 | Bruna ...................... 235/91 R |
| 6,161,724 A * | 12/2000 | Blacker et al. ................ 222/23 |
| 6,164,494 A | 12/2000 | Marelli | |
| 6,953,039 B2 * | 10/2005 | Scarrott et al. ........ 128/200.14 |

FOREIGN PATENT DOCUMENTS

| | | |
|---|---|---|
| EP | 0 480 488 | 4/1992 |
| EP | 1 065 477 | 1/2001 |
| GB | 1 317 315 | 5/1973 |

(Continued)

*Primary Examiner*—Lien M. Ngo
(74) *Attorney, Agent, or Firm*—Smith, Gambrell & Russell LLP

(57) ABSTRACT

Apparatus comprising a housing (1) defining a portion (2) for receiving in use a dose-dispensing container (20), the housing containing a dose counter comprising at least one annular counter member (241, 242) and a helix-like coil (243), wherein one or more projections (255) are provided on the helix-like coil for operatively connecting the helix-like coil and the at least one annular counter member, wherein movement of the received dose-dispensing container acts to compress the helix-like coil to thereby rotate the at least one annular counter member.

20 Claims, 2 Drawing Sheets

FOREIGN PATENT DOCUMENTS

Figure 1:
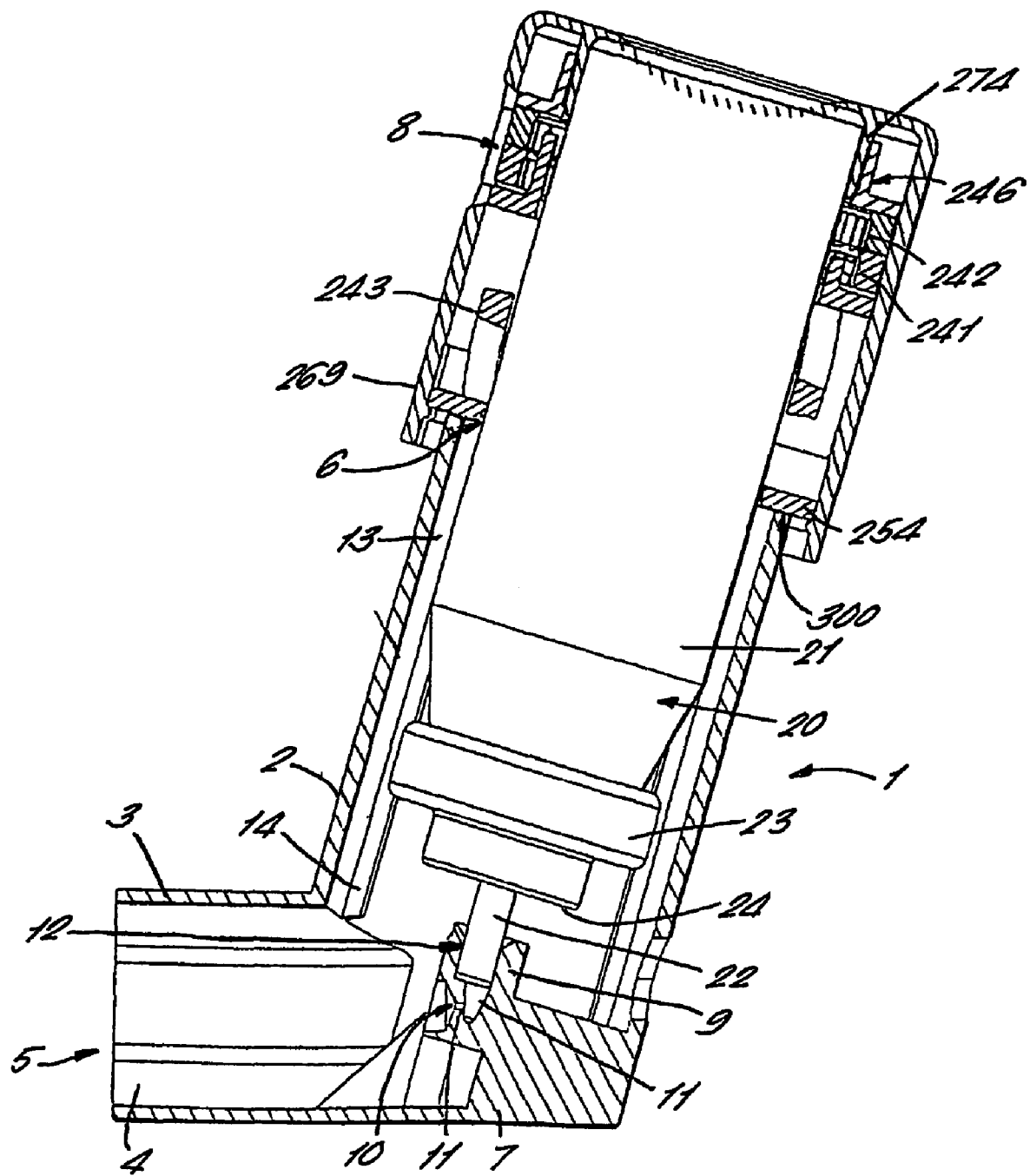

| | | |
|---|---|---|
| GB | 2 372 541 | 8/2002 |
| GB | 2 372 542 | 8/2002 |
| GB | 2 372 543 | 8/2002 |
| WO | WO 95/08484 | 3/1995 |
| WO | WO 02/069252 | 9/2002 |
| WO | WO 02/069253 | 9/2002 |

* cited by examiner

DOSAGE COUNTING DEVICES

The present invention relates to counting devices for use with dose-dispensing delivery apparatus which require an axial force for operation.

It has been recognised that there is a need to provide accurate information to the user of a dose-dispensing delivery apparatus concerning the number of doses delivered from, or remaining in, the apparatus. Without such accurate information there is the danger that a user will forget how many doses have been delivered and hence take a greater or fewer number of doses than is required. There is also the danger that a user may be unaware that the delivery apparatus is empty or close to empty. Hence, in an emergency situation, the user may seek to take a dose from the delivery apparatus only to find that there are no doses left in the apparatus. This is especially dangerous where the delivery apparatus is for use in dispensing medicinal compounds for the treatment of chronic or acute symptoms, for example, as in the case of a pressurised metered dose inhaler used for treating asthmatic reactions.

A number of devices have been proposed to count the number of doses delivered or remaining in a delivery apparatus. WO95/08484 teaches a dose counting device for use with an aerosol medication dispenser. The device works by translating a non-rotative force on an outer cover into a rotation of an indicator wheel by use of a set of flexible pawls engaged with a set of teeth. The pawls depress and thereby extend circumferentially when the applied force forces them to effect a rotation of the teeth. This device has, however, been found to have disadvantages. The reliability of operation of the counting device depends on the relationship between the stiffness of the internal spring bias of the medication dispenser and the pawls. If the pawls are too stiff relative to the internal spring bias then the medication dispenser may dispense a dose before the pawls flex sufficiently to rotate the indicator wheel; a dose wold be delivered without the counter registering it. Alternatively, if the pawls are too flexible relative to the internal spring bias then the pawls may flex sufficiently to rotate the indicator wheel before the medication dispenser has dispensed a dose; a dose would be registered by the counter but not actually delivered.

The present invention seeks to provide a dosage counting device which overcomes these problems.

Accordingly, the present invention provides apparatus comprising a housing defining a portion for receiving in use a dose-dispensing container, the housing containing a dose counter comprising at least one annular counter member and a helix-like coil, wherein one or more projections are provided on the helix-like coil for operatively connecting the helix-like coil and the at least one annular counter member, wherein movement of the received dose-dispensing container acts to compress the helix-like coil to thereby rotate the at least one annular counter member.

The present invention also provides apparatus comprising a housing defining a portion for receiving in use a dose-dispensing container, the housing containing a dose counter comprising at least one annular counter member, a helix-like coil having one or projections for operatively connecting the helix-like coil and the at least one annular counter member, and a support for supporting the at least one annular counter member and helix-like coil in proper alignment with the received dose-dispensing container, wherein the support is an interference fit in a cap of the housing such that a first actuation of the received dose-dispensing container sets the position of the support relative to the received dose-dispensing container and cap.

Figure 2:
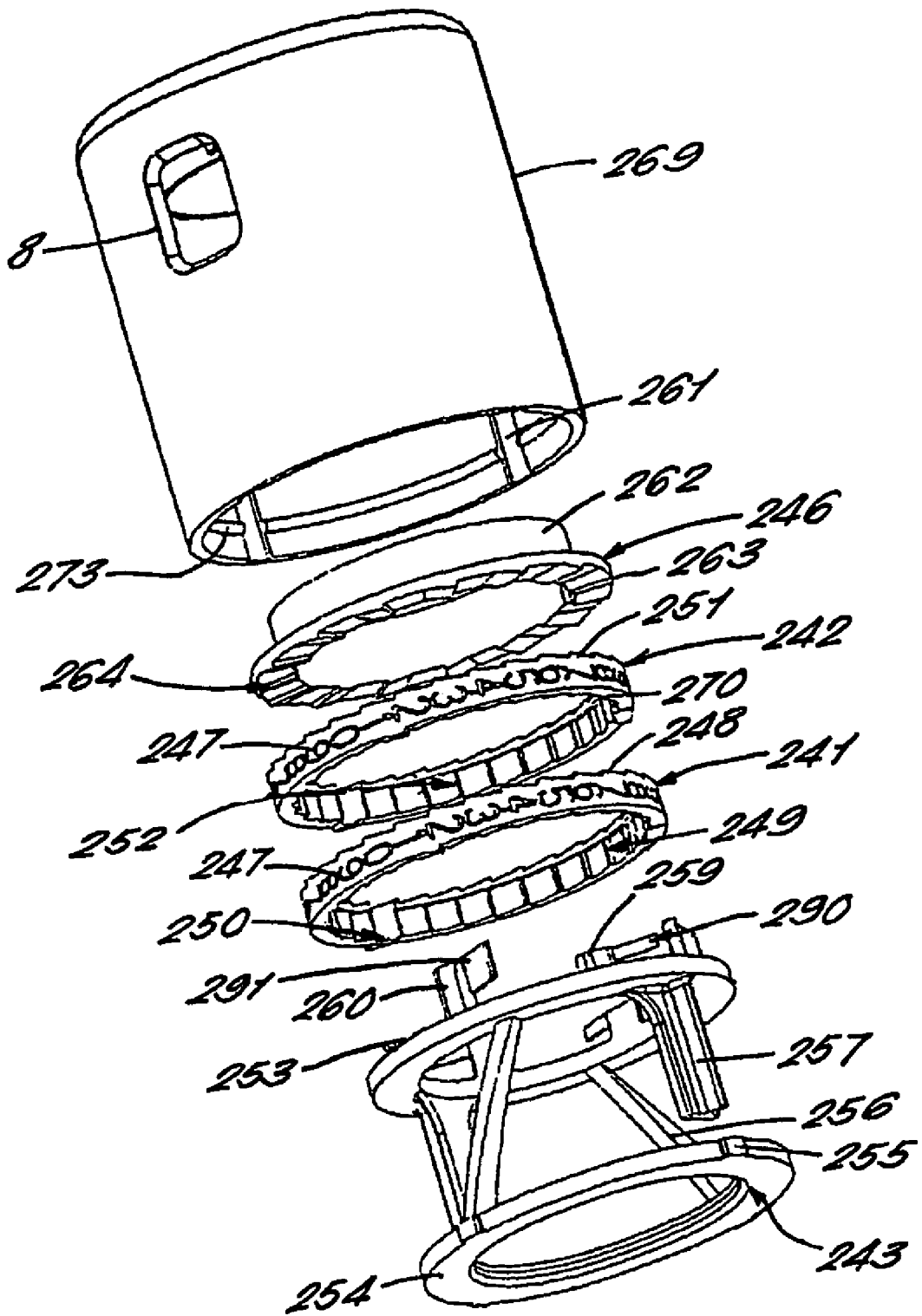

An embodiment of the present invention will now be described, by way of example only, with reference to the accompanying drawings, in which:

FIG. 1 is a cross-sectional view of a dispensing apparatus according to the present invention; and FIG. 2 is an exploded perspective view of part of the dispensing apparatus of FIG. 1.

In the following description, the invention will be illustrated, by way of example only, with respect to a pressurised dispensing container capable of delivering successive doses of a product in an aerosol form.

FIGS. 1 and 2 illustrate a dispensing apparatus according to the present invention.

The dispensing apparatus comprises a housing 1 having a cylindrical portion 2 with upper and lower ends. The upper end 6 is open whilst the lower end is closed off by a basal wall portion 7. A mouthpiece 3 which communicates with the cylindrical portion 2, depends laterally from the lower end of the cylindrical portion 2. The mouthpiece 3 defines an outlet duct 4 which terminates in an outlet 5 of the mouthpiece 3.

An inwardly directed valve stem receiving block 9 is integrally formed with the basal wall portion 7 and has its longitudinal axis aligned co-axially with a longitudinal axis of the cylindrical portion 2 of the housing 1. The valve stem receiving block 9 defines a receiving bore 12 which is open to the cylindrical portion 2 and an orifice 10 which is open to the outlet duct 4 of the mouthpiece 3. The receiving bore 12 and orifice 10 are linked by a duct 11.

Several, preferably six circumferentially spaced inwardly directed longitudinal ribs 14 are provided on the internal wall of the cylindrical portion 2.

In use a pressurised dispensing container 20 is received in the cylindrical portion 2. The pressurised dispensing container 20 comprises a canister body 21 defining a storage chamber for housing the product to be dispensed. The canister body 21 is closed off at one end by a metering valve (not shown) having a valve stem 22 which extends externally from the metering valve. The metering valve is retained in the canister body by a crimped ferrule 23.

When the pressurised dispensing container 20 is inserted into the housing 1, the valve stem 22 is received in receiving bore 12 of the valve stem receiving block 9. An annular air gap 13 exists between the internal wall of the cylindrical portion 2 and the canister body 21 to allow air to flow through the dispensing apparatus in use.

According to the present invention a dosage counter is provided comprising first and second indicator wheels 241, 242, a helical coil 243 and support 246. The first and second indicator wheels 241, 242 comprise indicia 247 marked on their peripheral walls. The first indicator wheel 241 denotes numerical 'units' and the second indicator wheel 242 denotes numerical 'tens'. Each indicator wheel 241, 242 is annular.

The upper rim of the first indicator wheel 241 is formed into a series of teeth which will be denoted as the upper teeth 248 of the first indicator wheel 241. In addition, the first indicator wheel 241 comprises a series of internal teeth 249 arranged around a lower portion of the internal rim of the annulus. The first indicator wheel 241 also comprises three evenly distributed radial notches 250 on the upper half of the internal rim of the annulus. Alternatively, two or more than three notches 250 may be provided.

The lower rim of the second indicator wheel 242 is formed into a series of teeth which will be denoted as the lower teeth 270 of the second indicator wheel 242. The upper rim of the second indicator wheel 242 is formed into a series of teeth which will be denoted as the upper teeth 251 of the second indicator wheel 242. In addition, the second indicator wheel 242 comprises a series of internal teeth 252 arranged around a lower portion of the internal rim of the annulus.

The support 246 comprises an annular portion 262 from which depends an annular flange 263 whose lower face is formed into a series of teeth which will be denoted as the lower teeth 264 of the support 246.

The helical coil 243 comprises an upper ring 253 and a lower-ring 254 which are interconnected by two flexible helical struts 256. The lower ring 254 comprises four equi-spaced radially outwardly directed protrusions 255. The upper ring 253 is provided with at least one pair of upper and lower arms 260, 259 extending upwardly therefrom. Each arm is provided with a laterally dependent finger portion forming a pawl which selectively engages the internal teeth 249, 252 of the first and second indicator wheels 241, 242 as described below. Two vertical struts 257 depend from the upper ring 253 and extend partially towards the lower ring 254.

The first and second indicator wheels 241, 242, helical coil 243 and support 246 are assembled within a cap 269. The cap 269 is generally cylindrical in shape and is closed off at an upper end. A window 8 is formed in a side wall near the upper end. Four longitudinally directed recesses 261 are formed equi-spaced around the internal surface of the cap 269. An annular inwardly directed rim 273 is provided near the open end of the cap 269.

The dosage counter is assembled by first inserting the support 246 into the cap 269. The support 246 forms a push-fit with the internal wall of the cap 269. The second indicator wheel 242, first indicator wheel 241 and helical coil 243 are then inserted into the cap 269 in that order. The four protrusions 255 of the lower ring 254 are received in the longitudinal recesses 261 of the cap 269. The components of the dosage counter are retained within the cap 269 by the interference of the lower ring 254 of the helical coil 243 and the annular rim 273 of the cap 269.

In the assembled position, the fingers 290 of the lower arms 259 of are aligned with the internal teeth 249 of the first indicator wheel 241. The fingers 291 of the upper arms 260 are partially aligned with the internal teeth 252 of the second indicator wheel 242 and partially aligned with the upper half of the internal rim of the first indicator wheel 241. Hence, the fingers 290 of the lower arms 259 are always engaged with the internal teeth 249 of the first indicator wheel 241 but the fingers 291 of the upper arms 260 are normally held out of engagement with the internal teeth 252 of the second indicator wheel 242 due to the presence of the internal rim of the first indicator wheel 241.

The pressurised dispensing container 20 is received in the housing 1. The cap 269 is then placed over the upper end of the pressurised dispensing container 20. A tubular extension 274 is provided within the cap 269 into which the canister body 21 forms a push-fit so as to retain the cap 269 in engagement with the housing 1. With the cap 269 engaged with the housing 1, the lower ring 254 abuts and rests on the upper end 6 of the cylindrical portion 2 of the housing 1 against the upper rim 300.

In use, a user operates the pressurised dispensing container 21 by depressing the closed end of cap 269 axially to move it and the canister body 21 relative to the cylindrical portion 2 of the housing 1. As a result, the valve stem 22 is inwardly retracted relative to the metering valve such that a dose of product is dispensed from the valve stem 22 into the bore 12 and duct 11 of the valve stem receiving block 9. The product is then channelled by duct 11 and dispensed as an aerosol through orifice 10 into the outlet duct 4. The aerosol is inhaled by a user inhaling on outlet 5 of the mouthpiece 3. The support 246 is a push-fit within the cap 269 and therefore does not move axially during a normal operating cycle. Axial movement of the cap 269 causes the lower ring 254 to be compressed towards the upper ring 253 of the helical coil 243. At the same time, due to the helical struts 256, the upper ring 253 rotates relative to the lower ring 254 which cannot rotate relative to the cap 269 due to the engagement of the protrusions 255 in the longitudinal recesses 261. The embodiment shown in FIG. 1 further shows helical coil 243 being dimensioned to encircle and axially receive dose-dispensing container 21.

As the upper ring 253 rotates, the first indicator wheel 241 is incrementally rotated due to engagement of the fingers 290 of the lower arms 259 with the internal teeth 249.

The degree of axial movement of the upper ring 253 relative to the lower ring 254 is limited by the vertical struts 257 which ground against the lower ring 254.

After successive rotations of the first indicator wheel 241 the fingers 291 of the upper arms 260 are brought into alignment with the radial notches 250 of the first indicator wheel 241. As a consequence, the fingers 291 of the upper arms 160 can flex radially outwards so as to engage the internal teeth 252 of the second indicator wheel 242. Consequently, the second indicator wheel 242 rotates one increment on the next actuation of the metering valve. In this way, the 'tens' indicia can be incremented once for every ten increments of the 'units' indicia.

On release of the canister body 21 by the user, the pressurised dispensing container 20 returns to its rest position as described above. At the same time, the helical coil 243 recovers to its original shape. The angling of the fingers 290, 291 of the upper and lower arms 260, 259, and the teeth of the support 246 and first and second indicator wheels 241, 242 prevents any reverse movement of the indicator wheels 241, 242 during this part of the operating cycle.

The dosage counter is 'set' in the cap 269 on the first actuation as follows:

The support 246 is assembled in the cap 269 at a point below its normal operating position, i.e., nearer the open end of the cap than shown in FIG. 1.

Consequently, the first and second indicator wheels 241, 242 and helical coil 243 are all also nearer the open end than their normal operating positions. On the first actuation, which may be undertaken by the user or at the point of manufacture or sale, the upper rim 300 at the upper end 6 of the housing 1 initially compresses the helical coil 243 without moving the support 246. Once the helical coil 243 has been compressed such that the vertical struts 257 have contacted the lower ring 254 (during which movement the metering valve is actuated), the user, pharmacist or manufacturer applies a higher axial force to the cap 269 to move both the helical coil 243 and support 246 axially relative to the cap 269 until the retracted valve stem 22 'grounds' against the base of the receiving bore 12 of the valve stem receiving block 9. The support 246 is now in its normal operating position and is 'set'. The setting of the support 246 takes into account any variations in distance between the upper rim 300 at the upper end 6 of the housing 1 and the end of the valve stem 22. Without this feature, it is possible for variations in pressurised dispensing containers to mean that in certain circumstances, the metering valve may be actuated before the first indicator wheel 241 rotates or vice versa.

The invention claimed is:

1. Apparatus comprising a housing defining a portion for receiving in use a dose-dispensing container, the housing containing a dose counter comprising at least one annular counter member and a helix-like coil, wherein one or more projections are provided on the helix-like coil for operatively connecting the helix-like coil and the at least one annular counter member, wherein movement of the received dose-dispensing container acts to compress the helix-like coil to thereby rotate the at least one annular counter member, and wherein each of the at least one annular counter members comprise a first series of teeth, the one or more projections of the helix-like coil being selectively engagable with each of the first series of teeth such that rotational movement of the helix-like coil causes the at least one annular counter member to rotate relative to the housing in a first direction.

2. Apparatus as claimed in claim 1 wherein the helix-like coil comprises an upper ring, a lower ring and at least one strut spanning between the upper and lower rings.

3. Apparatus as claimed in claim 2 wherein the at least one strut is helically shaped.

4. Apparatus as claimed in claim 2 or claim 3 wherein one of the upper or lower rings of the helix-like coil comprises one or more projections orientated towards the other of the upper or lower rings to thereby limit the movement of the upper and lower rings towards one another.

5. Apparatus as claimed in claim 1 wherein the first series of teeth are formed around an inner rim of the at least one annular counter members.

6. Apparatus as claimed in claim 1 wherein the dose counter comprises two or more annular counter members.

7. Apparatus as claimed in claim 1 wherein the housing comprises a cap.

8. Apparatus as claimed in claim 7 further comprising a support slidably received in the cap to support the at least one annular counter member and helix-like coil in proper alignment.

9. Apparatus as claimed in claim 7 wherein the lower ring of the helix-like coil contacts an upper end of the dose-dispensing container receiving portion of the housing.

10. Apparatus as claimed in claim 8 wherein a surface of the support is formed into a series of teeth engagable with a second series of teeth formed on a second annular counter member, so as to prevent rotation of the annular counter members in a direction opposed to the first direction.

11. Apparatus as claimed in claim 1 wherein the helix-like coil comprises at least one ratchet engagable with the first series of teeth formed on each of the annular counter members, so as to prevent rotation of the annular counter members in a direction opposed to the first direction.

12. Apparatus as claimed in claim 11 wherein a bearing surface is provided forming at least part of the inner rim of the first annular counting member to selectively hold the projections out of engagement with the first series of teeth of a second annular counter member, the bearing surface comprising at least one indent allowing movement of the projections radially outwardly into engagement with the first series of teeth of the second annular counter member after a pre-determined number of incremental rotations of the first annular counter member.

13. Apparatus as claimed in claim 6 wherein the first annular counter member is driven to incrementally rotate in the first direction on each actuation of the received dose-dispensing container and a second annular counter member is driven to incrementally rotate in the first direction only after a pre-determined number of incremental rotations of the first annular counter member.

14. Apparatus comprising a housing defining a portion for receiving in use a dose-dispensing container, the housing containing a dose counter comprising at least one annular counter member, a helix-like coil having one or more projections for operatively connecting the helix-like coil and the at least one annular counter member, and a support for supporting the at least one annular counter member and helix-like coil in proper alignment with the received dose-dispensing container, wherein the support is an interference fit in a cap of the housing such that a first actuation of the received dose-dispensing container sets the position of the support relative to the received dose-dispensing container and cap.

15. Apparatus comprising a housing defining a portion for receiving in use a dose-dispensing container, the housing containing a dose counter comprising at least one annular counter member and a helix-like coil, wherein one or more projections are provided on the helix-like coil for operatively connecting the helix-like coil and the at least one annular counter member, wherein movement of the received dose-dispensing container acts to compress the helix-like coil to thereby rotate the at least one annular counter member, and wherein one of the upper or lower rings of the helix-like coil comprises one or more projections orientated towards the other of the upper or lower rings to thereby limit the movement of the upper and lower rings towards one another.

16. Apparatus comprising a housing defining a portion for receiving in use a dose-dispensing container, the housing containing a dose counter comprising at least one annular counter member and a helix-like coil, wherein one or more projections are provided on the helix-like coil for operatively connecting the helix-like coil and the at least one annular counter member, wherein movement of the received dose-dispensing container acts to compress the helix-like coil to thereby rotate the at least one annular counter member, and wherein the housing comprises a cap, and wherein the lower ring of the helix-like coil contacts an upper end of the dose-dispensing container receiving portion of the housing.

17. Apparatus comprising a housing defining a portion for receiving in use a dose-dispensing container, the housing containing a dose counter comprising at least one annular counter member and a helix-like coil, wherein one or more projections are provided on the helix-like coil for operatively connecting the helix-like coil and the at least one annular counter member, wherein movement of the received dose-dispensing container acts to compress the helix-like coil to thereby rotate the at least one annular counter member, and wherein the housing comprises a cap, and said apparatus further comprising a support slidably received in the cap to support the at least one annular counter member and helix-like coil in proper alignment, and wherein a surface of the support is formed into a series of teeth engagable with a second series of teeth formed on a second annular counter member, so as to prevent rotation of the annular counter members in a direction opposed to the first direction.

18. Apparatus comprising a housing defining a portion for receiving in use a dose-dispensing container, the housing containing a dose counter comprising at least one annular counter member and a helix-like coil, wherein one or more projections are provided on the helix-like coil for operatively connecting the helix-like coil and the at least one annular counter member, wherein movement of the received dose-dispensing container acts to compress the helix-like coil to thereby rotate the at least one annular counter member, and wherein said helix-like coil is dimensioned to encircle and axially receive the dose-dispensing container.

19. Apparatus as claimed in claim 1 wherein a bearing surface is provided forming at least part of an inner rim of a first annular counting member to selectively hold the one or more projections out of engagement with the first series of teeth of a second annular counter member, the bearing surface comprising at least one indent allowing movement of the projections radially outwardly into engagement with the first series of teeth of the second annular counter member after a pre-determined number of incremental rotations of the first annular counter member.

20. Apparatus as claimed in claim 18 wherein each of the at least one annular counter members comprise a first series of teeth, the one or more projections of the helix-like coil being selectively engagable with each of the first series of teeth such that rotational movement of the helix-like coil causes the at least one annular counter member to rotate relative to the housing in a first direction.

* * * * *